United States Patent [19]

Murphy

[11] Patent Number: 5,227,797

[45] Date of Patent: * Jul. 13, 1993

[54] RADAR TOMOGRAPHY

[76] Inventor: Quentin M. Murphy, 29 Homesdale Rd., Bronxville, N.Y. 10708

[*] Notice: The portion of the term of this patent subsequent to Jul. 9, 2008 has been disclaimed.

[21] Appl. No.: 704,610

[22] Filed: May 23, 1991

Related U.S. Application Data

[62] Division of Ser. No. 342,816, Apr. 25, 1989, Pat. No. 5,030,956.

[51] Int. Cl.$^5$ .................. G01S 13/04; G01S 13/06
[52] U.S. Cl. ..................... 342/22; 128/777; 128/653.1
[58] Field of Search ............ 342/22, 179, 180, 190; 378/4, 38, 210; 433/25; 128/653 R, 777

[56] References Cited

U.S. PATENT DOCUMENTS

| | | |
|---|---|---|
| 2,283,935 | 5/1942 | King . |
| 2,985,880 | 5/1961 | McMillan . |
| 3,124,798 | 3/1964 | Zinke . |
| 3,307,186 | 2/1967 | Straub . |
| 3,663,932 | 5/1972 | Mount et al. . |
| 3,713,156 | 1/1973 | Pothier . |
| 3,886,561 | 5/1975 | Beyer . |
| 4,091,385 | 5/1978 | Petlevich et al. . |
| 4,119,932 | 10/1978 | Bockrath . |
| 4,156,481 | 4/1981 | Mawhinney . |
| 4,486,835 | 12/1984 | Bai et al. . |
| 4,493,039 | 1/1985 | Gregory . |
| 4,539,640 | 9/1985 | Fry et al. . |
| 4,546,649 | 10/1985 | Jenson . |
| 4,558,425 | 12/1985 | Yamamoto et al. . |
| 4,562,540 | 12/1985 | Devaney . |
| 4,653,000 | 3/1987 | Matsumoto . |
| 4,674,513 | 6/1987 | Jasper, Jr. . |
| 4,689,675 | 8/1987 | Tchurbajian et al. . |
| 4,712,559 | 12/1987 | Turner . |
| 4,749,973 | 6/1988 | Kaneko et al. . |
| 4,768,156 | 8/1988 | Whitehouse et al. ............ 342/195 X |
| 4,780,661 | 10/1988 | Bolomey et al. . |
| 4,837,578 | 6/1989 | Gammell . |
| 4,886,069 | 12/1989 | O'Donnell . |
| 4,896,033 | 1/1990 | Gautier . |
| 4,915,498 | 4/1990 | Malek ............................ 342/94 X |
| 4,926,868 | 5/1990 | Larsen . |
| 4,930,513 | 6/1990 | Mayo et al. . |
| 4,937,580 | 6/1990 | Wills ............................. 342/22 |
| 4,958,638 | 9/1990 | Sharpe et al. . |
| 5,030,956 | 7/1991 | Murphy .......................... 342/22 |

*Primary Examiner*—Mark Hellner
*Attorney, Agent, or Firm*—Fitzpatrick, Cella, Harper & Scinto

[57] ABSTRACT

A radar tomography method and apparatus usable in industrial applications emits a plurality of radar pulses toward an adjacent object. A transmitter provides the plurality of radar pulses to the antenna, and a receiver receives the plurality of reflected radar pulses which correspond to the emitted plurality of radar pulses reflected from internal structure within the object. Timer/gate means selects predetermined radar pulses from among the received radar pulses, the selected radar pulses corresponding to a predetermined area of interest within the object. The selected radar pulses include pulses which represent internal structure of interest and pulses which represent internal structure which is contiguous to the internal structure of interest. The selected pulses include information which discriminates the internal structure of interest from the contiguous internal structure.

38 Claims, 2 Drawing Sheets

MATRIX FILTER

RADAR TOMOGRAPHY

This application is a continuation division of application Ser. No. 07/342,816 filed Apr. 25, 1989 now U.S. Pat. No. 5,030,956.

BACKGROUND OF THE INVENTION

The present invention relates to medical imaging apparatus and method, and particularly to tomography utilizing radar pulses.

A variety of medical imaging modalities are known and include nuclear magnetic resonance, ultra-sound, sonography, positron emission, digital subtraction angiography, and x-rays. Computed tomography is a well-known method for manipulating data to produce medical images. For example, ultra-sound, positron emission, and X-rays may utilize computed tomography techniques to produce images for diagnosis. A recent article, "III Imaging With Photons", by Edward Rubenstein, appearing in the December, 1988, edition of CURRENT TRENDS IN MEDICINE, explains several of these imaging methods and is incorporated herein by reference.

However, all known medical imaging modalities are considered to be either too expensive or may be at least somewhat harmful to the patient. For example, a nuclear magnetic resonance machine may cost $2.5 million and require almost one-thousand dollars to produce an image. On the other hand, the use of X-rays is disadvantageous in that repeated use may result in harm to the patient.

Furthermore, known imaging techniques can create an image by passing energy through the patient to produce a projected image or a cross-sectional image of the patient. The power required to pass certain types of energy and energized particles through a patient is expensive to produce and may cause harm to patient tissue.

Thus, the medical practitioner often is presented with the dilemma of choosing between the desire to perform a thorough diagnosis and excessive cost or patient harm resulting from such thorough diagnosis. In fact, medical insurance companies are demanding greater use of medical imaging equipment, while patients are being informed by the media and various consumer advocates that increased use of, for example, X-rays is unnecessary and harmful. Therefore, medical personnel are placed in the difficult position of trying to satisfy both their patient's needs and their insurer's requirements.

Accordingly, what is needed is a simple, fast, low-cost medical imaging technique which causes no harm to the patient.

It is known that radio waves will penetrate human tissue, and that radio wavelengths of electromagnetic radiation are considered non-ionizing, thus causing no radiation damage. For example, current technologies employ short-wave and microwave radiation to treat deep muscle injury with controlled heat. No tissue damage occurs even when the radio waves are applied steadily for periods of up to 30 minutes. U.S. Food and Drug Administration (FDA) guidelines for use of such modalities are currently available. Furthermore, radar technology is relatively well developed in military and civilian aviation. In addition, the proliferation of radar guns and related equipment in traffic enforcement is well-known.

Radar uses a wavelength of several meters to several millimeters. Radar can also be focused into more concentrated beams than X-rays. In addition, sensitive radar receivers are available which can image an object at great distances registering a small fraction of the radiated energy. Radar also produces an image by reflecting energy from an object, thus requiring less power and producing less tissue damage in the patient than known techniques. Thus, it appears that radar signals may be useful in medical imaging.

SUMMARY OF THE INVENTION

An object of the present invention is to provide a medical imaging method and apparatus utilizing radar signals.

In order to achieve the above object, the present invention is directed to a method and apparatus for emitting a plurality of radar or radio pulses toward a subject with an antenna, providing the radar pulses to the antenna with a transmitter, and receiving the plurality of radar pulses reflected from the subject with a receiver. A timer/gate circuit is used to select predetermined radar pulses from among the received, reflected radar pulses. The radio pulses selected are those which correspond to a predetermined area, at a predetermined depth, of interest within the subject.

Preferably, the timer/gate circuit can be controlled in order to scan the predetermined area throughout the subject.

If desired, a three-dimensional image of a predetermined volume within the subject can be produced by generating relative movement between the antenna and the subject. This produces a sequence of scans at differing depths within the target volume within the patient. A processor then stores and manipulates the view data in order to produce a three-dimensional view of the predetermined volume within the subject.

In order to more accurately focus the emitted and reflected radar pulses, the present invention may include a matrix filter, coupled to the antenna, which reduces noise by eliminating unwanted reflection and diffraction components. The matrix filter may include a plurality of radar absorbing tubes disposed to form a grid in cross-section.

Of course, the present invention may also include display means for displaying the predetermined two and three-dimensional areas within the subject.

The advantageous structure and functions according to the present invention will become readily apparent to those of ordinary skill in this art from the following detailed description of the preferred embodiment, taken together with the accompanying drawing.

DETAILED DESCRIPTION OF THE PREFERRED EMBODIMENT

The principle of radar is relatively simple. Radio wave energy is emitted toward an object and its position and relative movement may be determined through the return radio echo. The frequency of the radio pulses and the intensity of each pulse may be varied in accordance with the type of echo desired, the relative distance to and movement of the subject, and the type of antenna used. From the return echo, the distance to the object may be readily calculated by well-known Doppler techniques. The signal-to-noise (SNR) ratio of the return echo pulses may be diminished by resonance, diffraction, or off-phase interference. Techniques for reducing resonance (artificial wave amplification), and off-phase interference are well-known and could be implemented in the present invention.

Diffraction may reduce the SNR by causing scattering of the return pulses into the receiver. As will be discussed below, the present invention proposes a matrix filter in order to reduce diffraction noise.

Producing a medical image from the return echo pulses can be a matter of applying existing technology. Well-known computed tomography techniques may be used to process the return radar signals in order to produce usable images for medical diagnosis. For example, a timer/gate device may be used to gate the receiver so that it receives only pulses from a selected distance. Another technique is to utilize a so-called range filter in which a plurality of range bins are disposed. A return radar signal entering a particular range bin indicates that the subject is at a predetermined distance from the antenna. Such techniques are known in the radar field and need not be described in greater detail herein.

Figure 1:
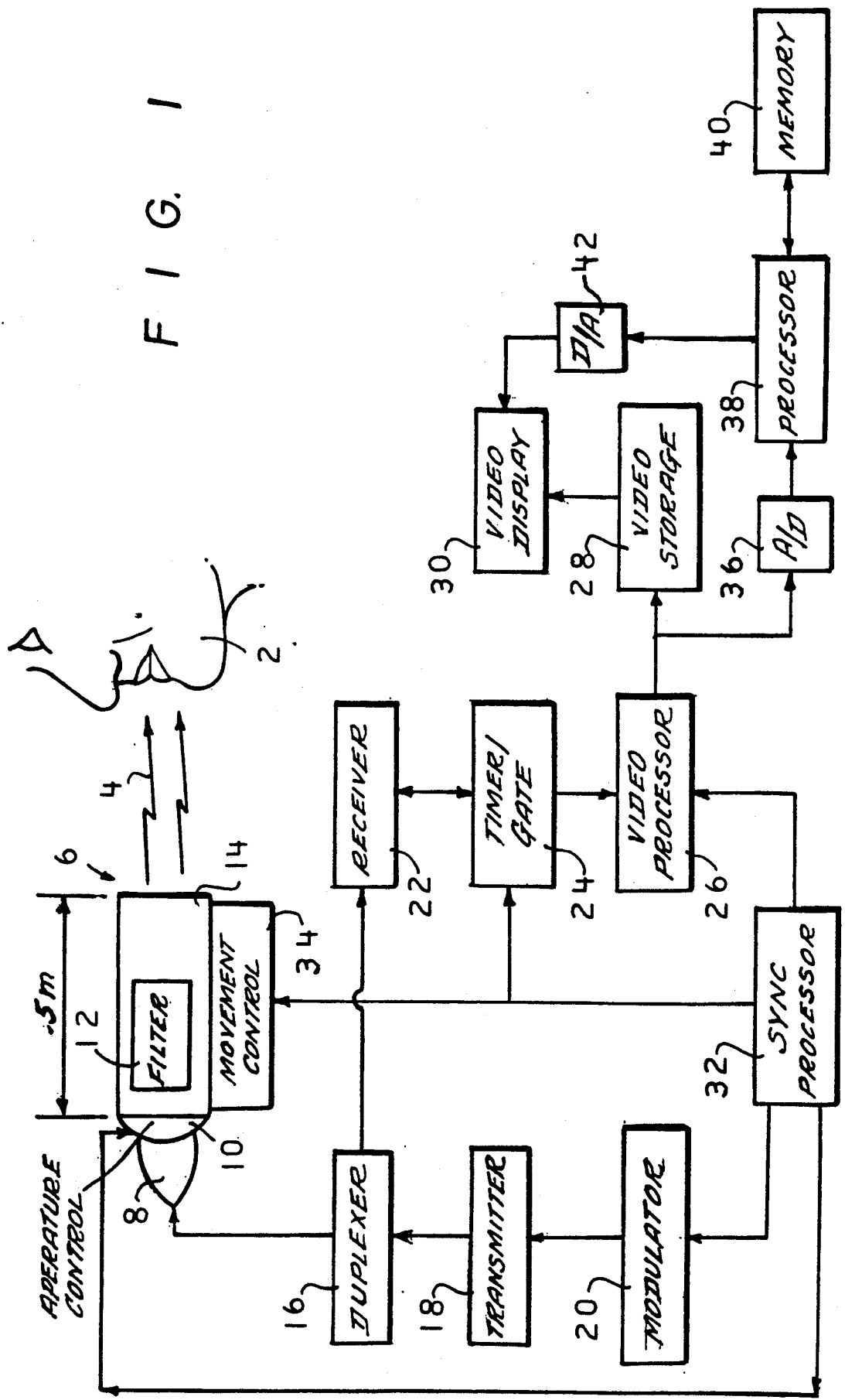
FIG. 1 is a schematic block diagram of the apparatus according to the preferred embodiment.

Referring now more particularly to the drawing, FIG. 1 is a block diagram of a preferred embodiment of the present invention. This embodiment is a radar tomography device adapted for use in dentistry to examine a patent's teeth, although the principles of the present invention may be adapted to a wide variety of medical imaging applications and devices.

In FIG. 1, the patient or subject 2 is exposed to pulsed radio signals 4 emitted from an antenna head 6. As schematically shown there, antenna head 6 includes an antenna 8, an aperture control device 10, a matrix filter 12, and a cone or cylinder spacer 14. A standard dental X-ray cone is usually 8 or 18 inches long, and therefore, an 18 inch cone or cylinder spacer 14 would be quite normal for use with the patient and by medical personnel. In addition, an 18 inch spacer 14 would provide approximately a 1 meter path for rays emitted from the antenna and reflected from the subject.

Antenna 8 may comprise any well-known or conventional radar antenna. For example, parabolic, Cassegrain, dipole, or flat semi-conductor antennas may be used. The antenna should be simple, light-weight, and inexpensive. The antenna should also be small enough to fit into the antenna head 6 and allow for ease of operation by medical personnel.

The aperture control device 10 is used to control the aperture of the antenna 8. This device 10 may include synthetic aperture control circuitry, or mechanical means such as two plates of radar-absorbing materials with slits moving in opposite directions allowing synchronous radiation emission and reception through one aperture at a time. Additionally, while the aperture control 10 is shown located between the antenna 8 and the filter 12, it may be located between the filter 12 and the patient 2. Again, such aperture control devices are relatively well-developed and need not be described in further detail here.

A matrix filter 12, as mentioned earlier, is used to reduce diffraction noise from the reflected return signal, and to properly focus the emitted signal on the area of the patient of interest. The matrix filter 12 may be designed in a predetermined pattern to correspond to the number of scans desired, and the location of the area of interest within the subject. A detailed description of one preferred embodiment of a matrix filter 12 will be provided below with reference to FIG. 2.

A duplexer 16 is provided to switch the antenna between a transmitting mode and a receiving mode. In the absence of the duplexer, the transmitted energy may harm a receiver 22 connected therethrough to receive the reflected radiation. Again, duplexers are very well known and are readily available. Of course, two antennae (one for transmitting, one for receiving) may be used in the present invention, thus eliminating the need for a duplexer.

A transmitter 18, also connected to the dupluxer 16, is a high-power oscillator which generates the radar pulses at a predetermined frequency, amplitude, and phase. A modulator 20 provides pulses of input power to activate the transmitter 18. For the duration of the input pulse from the modulator 20, the transmitter 18 generates a high-power radio frequency wave, converting a DC pulse to a pulse of radio frequency energy. The exact frequency of the emitted energy may be tuned to any appropriate range, as desired. The generated radio wave pulses are then transmitted to the antenna 8 through the duplexer 16.

The receiver 22 receives the reflected radar pulses from the antenna 8 through the duplexer 16. Typically, the receiver 22 is a superheterodyne receiver which translates the received signals from their frequency to a lower, intermediate frequency at which they can be filtered and amplified more conveniently. Translation is usually accomplished by adding the received signals to the output of a low-power local oscillator in a mixer. The output of the mixer is usually amplified and then filtered to reduce interfering signals, electrical background noise, resonance, and off-phase interference noise. Finally, the amplified received signals are output to a video processor 26 through a timer/gate 24 discussed below in detail. Radar receivers as described above are well known and need not be explained in further detail.

The timer/gate 24 is a device which selects predetermined pulses from among the received pulses in order to effect spatial control. For example, as the radar pulses are reflected back from the lower jaw of the patient 2, the timer/gate 24 selects only those return pulses timed to return from a desired depth (for example, 2 centimeters from the forward edge of radar head 6). Accordingly, only the gated pulses would be accepted for imaging. Preferably, timer/gate 24 controls the receiver 22 so that it only receives radar pulses from the desired location. By varying the return-plane distance within the patient by moving the antenna head toward or away from the volume of the patient under study, or by varying the time of acceptable pulse return, readings can be obtained for any desired tissue depth within the patent 2. The timer/gate 24 must be very sensitive since the patient 2 will be positioned close to the radar head 6. Timers capable of measuring picoseconds are now known. For example, such a timer identified by Model No. DG-535 is available from Stanford Research.

By moving radar head 6 relative to the patient 2, and then scanning in the depth direction through operation of the timer/gate 24, information may be derived in three-dimensions. Such techniques are well-known in the computed tomography field. This method will allow volumetric information to be obtained from the subject.

The video processor 26 receives the selected output from receiver 22 and processes the signal to produce a video signal capable of being stored in a video storage device 28, and/or displayed on video display 30. Apparatus such as the video processor 26, video storage 28, and video display 30, are known and available.

A synch processor 32 synchronizes the operation of the apparatus. Specifically, the transmitter 18 and video processor 26 are synchronized by generating a continuous stream of very short, evenly spaced pulses. They designate the times at which successive radar pulses are to be transmitted, and are supplied simultaneously to the modulator 20 and video processor 26. In addition, synch processor 32 controls timer/gate 24 to effect proper scanning control. Such synch processor are widely used in radar devices, and in computed tomography apparatus, and therefore, can be readily adapted to the present invention.

A high-resolution image of the area or volume of interest may also be obtained by providing relative movement between the antenna head 6 and subject 2. Thus, the movement control device 34 may be coupled to the antenna head 6 to move it with respect to patent 2. In a manner similar to a CATSCAN, the antenna head 6 may be moved in an arc around subject 2 in order to take several "shots" or "views" of the subject 2. In each view, the radar pulses are scanned in the X and Y directions by use of the aperture control 10, and in the depth direction by using the timer/gate 24. When information regarding the plurality of "views" is combined, a higher resolution image of the volume of interest may be obtained. Those having skill in this field will understand that the principles of image processing used in a CATSCAN device can be adapted to the present radar tomography device.

The signal output from the video processor 26 is an analog video signal capable of being stored on the video storage device 26 (for example, a VCR), or displayed on the video display device 30. However, digital techniques offer significant opportunities for image enhancement. Therefore, the analog signal from the video processor 26 may be provided to an analog-to-digital converter 36 to digitize the signal. The digitized signal is then provided to a digital processor 38 which can manipulate the data in a variety of well-known ways. For example, information from a plurality of "views", as discussed above, may be combined within the processor 38 to produce a high-resolution, three-color, three-dimensional view of a volume of interest within subject 2. Such images may then be converted to an analog signal by a digital-to-analog device 42 for display on the video display 30. The digital output from the processor 38 may also be provided to a memory 40 which stores the information for later retrieval and use. Imaging processors such as those used in nuclear magnetic resonance imaging may be adapted for use in the present invention.

Figure 2:
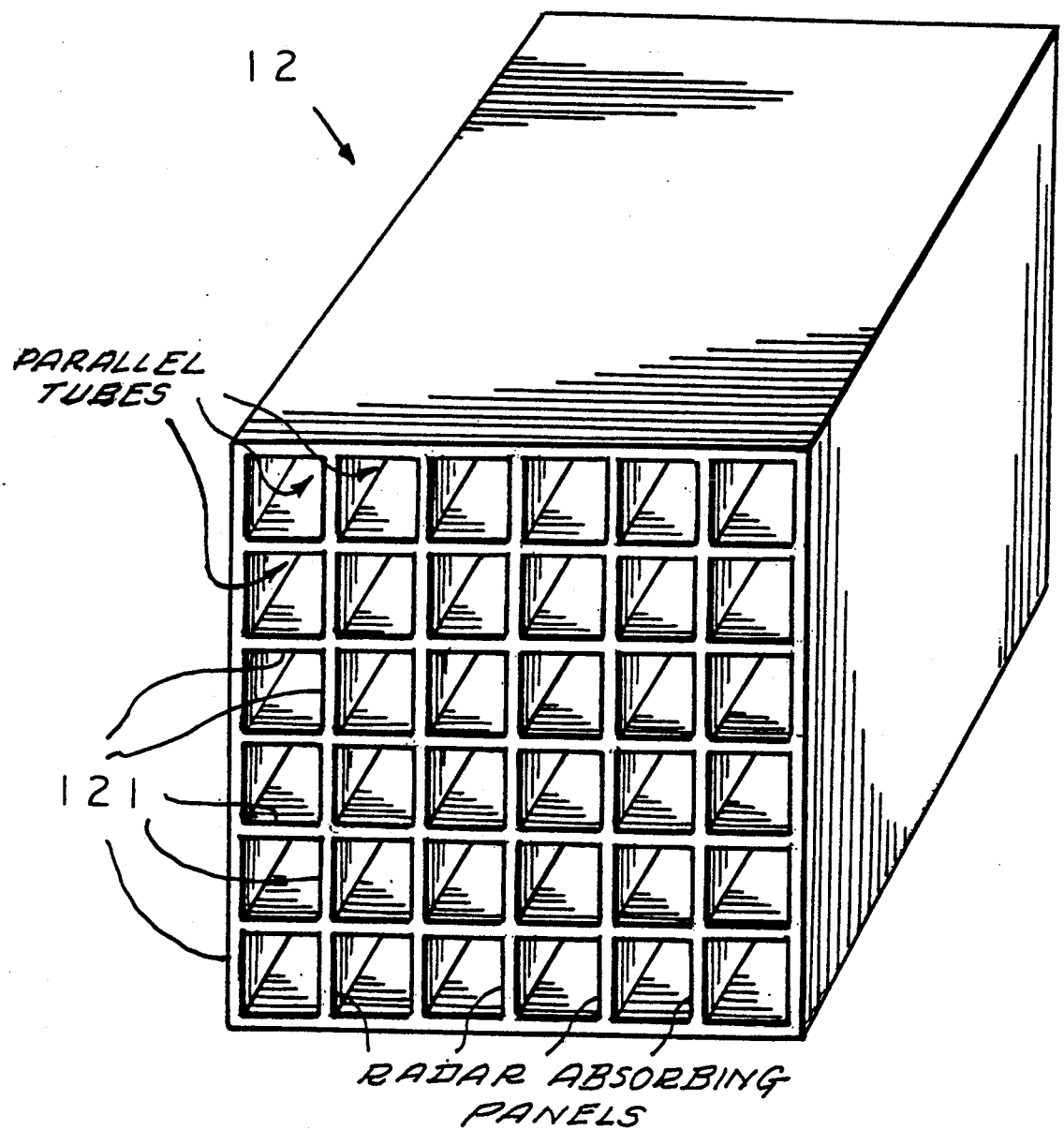
FIG. 2 is a perspective view showing the matrix filter of FIG. 1.

FIG. 2 is a perspective view of a preferred embodiment of the matrix filter 12. The matrix filter 12 has the dual function of focusing the emitted radar energy on the area of interest and eliminating diffraction noise from the reflected return pulses. Diffraction caused by scattering of the return waves is avoided by the size of the matrix filter 12. Matrix filter 12 is preferably a radar-absorbing 10 centimeter square parallel filtering box, broken into a cross-sectional grid of square tubes. The grid comprises a plurality of perpendicularly disposed radar-absorbing panels 121. The number and spacing of the panels may be modified somewhat, depending upon the desired radar frequency, phase, and power. Alternatively, the filter may be made of a matrix of parallel cylindrical tubes of radar-absorbing materials. Of course, the tubes may be of other cross-sectional shapes. Again, the design of such filters is fairly well developed in the radar field.

Thus, what has been described is a medical imaging modality using radar-frequency signals to produce inexpensive, high-resolution images of a subject. The apparatus utilizes existing technology, and therefore, should be relatively inexpensive to manufacture, market, and operate. Furthermore, medical insurers and patients alike will welcome such a safe, low-cost alternative to X-rays and nuclear magnetic resonance.

The specific structural details of the devices represented by blocks in the schematic diagram of FIG. 1 are per se well-known or could be readily constructed by the person of ordinary skill in this field without undue experimentation. Therefore, the exact structure of the blocks in the schematic is not described in detail in order to more clearly describe the present invention, and since such details are not critical to the best mode of carrying out the present invention.

While the present invention has been described with respect to what is presently considered to be the preferred embodiment, it is to be understood that the invention is not limited to the disclosed embodiment. To the contrary, the present invention is intended to cover various modifications and equivalent arrangements included within the spirit and scope of the appended claims. The scope of the following claims is to be accorded the broadest interpretation so as to encompass all such modifications and equivalent structure and functions.

What is claimed is:

1. A radar tomography apparatus, comprising:
    antenna means for emitting a plurality of radar pulses toward an adjacent object;
    transmitting means for providing the plurality of radar pulses to said antenna means;
    receiver means for receiving a plurality of reflected radar pulses which correspond to the emitted plurality of radar pulses reflected from internal structures within the object;
    timer/gate means for selecting predetermined radar pulses from among the received radar pulses, the selected radar pulses corresponding to a predetermined area of interest within the object, the selected pulses including pulses which represent internal structure of interest and pulses which represent internal structure which is contiguous to the internal structure of interest, the selected pulses including information which discriminates the internal structure of interest from the contiguous internal structure.

2. Apparatus according to claim 1, further including display means for displaying a representation of the predetermined area within the object based on the selected radar pulses.

3. Apparatus according to claim 2, wherein said display means comprises:
    a video processor for converting the selected radar pulses into a video signal; and
    a video display for receiving the video signal and displaying the representation of the predetermined area of the object.

4. Apparatus according to claim 3, further including:

an analog-to-digital circuit for converting the video signal from said video processor into a digital signal;

a digital processor for receiving the digital signal from said analog-to-digital circuit, processing the digital signal, and providing an output digital signal which corresponds to the predetermined area within the object; and a digital-to-analog circuit for converting the output digital signal into an analog signal for display on said video display.

5. Apparatus according to claim 4, further comprising memory means for receiving the output digital signal from said digital processor, storing the output digital signal, and providing a plurality of stored digital signals to said digital processor to cause said video display to display a plurality of predetermined areas within the object.

6. Apparatus according to claim 1, further including a matrix filter, coupled to said antenna means, for directing both the emitted radar pulses and the reflected radar pulses.

7. Apparatus according to claim 1, wherein said antenna means comprises:
a spacer head;
an antenna coupled to said spacer head;
an aperture control device for controlling an aperture of said antenna; and
a duplexer for switching said antenna between said transmitter means and said receiver means.

8. Apparatus according to claim 7, further including a matrix filter, coupled to said antenna, for directing the emitted radar pulses and the reflected radar pulses.

9. Apparatus according to claim 1, wherein said transmitter means comprises:
a transmitter for generating a plurality of generated radar pulses;
a modulator for modulating the generated radar pulses to produce the plurality of radar pulses provided to said antenna means; and
a synch processor for controlling the modulator to produce the plurality of radar pulses at predetermined timings.

10. Apparatus according to claim 9, further comprising a video processor for converting the selected radar pulses into a video signal; and
wherein said synch processor synchronizes operation of said modulator and said video processor.

11. Radar tomography apparatus, comprising:
an antenna for emitting a plurality of radar pulses toward an object, and for receiving a plurality of reflected radar pulses reflected from internal features within the object;
a filter for guiding the emitted and reflected pulses toward and from the object, respectively;
a transmitter for providing the plurality of radar pulses to said antenna;
a receiver for receiving the plurality of reflected radar pulses from said antenna;
a timer/gate circuit for selecting predetermined ones of the reflected radar pulses received by said receiver, the selected radar pulses corresponding to a predetermined area within the object, the selected pulses representing both internal structure of interest and internal structure contiguous to the structure of interest, the selected pulses discriminating between the internal structure of interest and the contiguous internal structure; and display circuitry for receiving the selected radar pulses from said timer/gate circuit and displaying a representation of the predetermined area within the object.

12. Apparatus according to claim 11, further comprising an aperture control device for controlling an aperture of said antenna.

13. Apparatus according to claim 12, further comprising a synch processor for synchronizing operation of said aperture control device, said transmitter, said timer/gate circuit, and said display circuitry.

14. Apparatus according to claim 11, wherein said filter comprises a box-like matrix structure having a plurality of radar-absorbing panels disposed horizontally and vertically therein.

15. Apparatus according to claim 11, wherein said display circuitry comprises:
a video processor for receiving the selected radar pulses from said timer/gate circuit and providing a video signal corresponding thereto; and
a video display for receiving the video signal from said video processor and displaying the predetermined area within the object.

16. Apparatus according to claim 11, further comprising movement means for producing relative movement between said antenna and the object, and wherein said receiver receives a plurality of sets of reflected radar pulses, and wherein said timer/gate circuit selects radar pulses from among each set, the selected pulses corresponding to a predetermined volume within the object.

17. Radar tomography apparatus, comprising:
an antenna for emitting a plurality of radar pulses toward an object, and for receiving a plurality of reflected radar pulses reflected from internal features within the object;
a filter, disposed between said antenna and the subject, for filtering the emitted and reflected radar pulses;
a duplexer for switching said antenna between a transmit mode and a receive mode;
a transmitter for providing the radar pulses to said antenna;
a receiver for receiving the reflected radar pulses from said antenna;
a timer/gate circuit for controlling said receiver to cause only radar pulses reflected from a predetermined area within the object to be received, the selected pulses representing both internal structure of interest and internal structure contiguous to the structure of interest, the selected pulses discriminating between the internal structure of interest and the contiguous internal structure; and
a processor for controlling said timer/gate circuit to cause said predetermined area to be scanned to different locations within the object.

18. Apparatus according to claim 17, further comprising display means for receiving the radar pulses corresponding to the predetermined area from said receiver, and for displaying a representation of the predetermined area.

19. Apparatus according to claim 17, further comprising movement means for producing relative movement between said antenna and the object, and wherein said transmitter provides a plurality of sets of radar pulses to said antenna, each set being emitted at a different position, and wherein said timer/gate circuit causes said receiver to receive only radar pulses reflected from a predetermined volume within the object.

20. Apparatus according to claim 19, further comprising processor means for (1) receiving the radar pulses corresponding to the predetermined volume from said receiver, (2) converting these received radar pulses to digital signals, (3) storing the digital signals, and (4) processing the stored digital signals to provide an output signal corresponding to a representation of the predetermined volume.

21. Radar tomography method, comprising the steps of:
   emitting a plurality of radar pulses toward an object, using an antenna;
   providing the plurality of radar pulses to said antenna;
   receiving a plurality of reflected radar pulses which correspond to the emitted plurality of radar pulses reflected from internal structure within the object; and
   selecting predetermined radar pulses from among the received radar pulses, the selected radar pulses corresponding to a predetermined area within the object, the selected pulses representing both internal structure of interest and internal structure contiguous to the structure of interest, the selected pulses discriminating between the internal structure of interest and the contiguous internal structure.

22. A method according to claim 21, further comprising the step of displaying a representation of the predetermined area within the object based on the selected radar pulses.

23. A method according to claim 22, wherein said display step comprises the steps of:
   converting the selected radar pulses into a video signal; and
   receiving the video signal and displaying the representation of the predetermined area of the subject.

24. A method according to claim 23, further comprising the steps of:
   converting the video signal into a digital signal;
   receiving the digital signal, processing the digital signal, and providing an output digital signal which corresponds to the predetermined area within the subject; and
   converting the output digital signal into an analog signal for display on a video display.

25. A method according to claim 24, further comprising the steps of:
   receiving the output digital signal;
   storing the output digital signal, and
   providing a plurality of stored digital signals to cause a plurality of predetermined areas within the object to be displayed.

26. A method according to claim 21, further comprising the steps of filtering the emitted radar pulses and the reflected radar pulses with a matrix filter.

27. A method according to claim 21, wherein said emitting step includes the step of:
   controlling an aperture of said antenna; and
   switching said antenna from a receive mode to a transmit mode.

28. A method according to claim 27, further including the steps of filtering the emitted radar pulses and the reflected radar pulses with a matrix filter.

29. A method according to claim 21, wherein said emitting step comprises the steps of:
   generating a plurality of generated radar pulses;
   modulating the generated radar pulses to produce the plurality of radar pulses provided to said antenna; and
   controlling the modulator to produce the plurality of radar pulses at predetermined timings.

30. A method according to claim 29, further comprising the step of converting the selected radar pulses into a video signal; and
   wherein said controlling step synchronizes said modulating step and said converting step.

31. Radar tomography method, comprising the steps of:
   emitting a plurality of radar pulses toward an object, and for receiving a plurality of reflected radar pulses reflected from internal features within the object, using an antenna;
   guiding the emitted and reflected pulses toward and from the object, respectively, using a filter;
   providing the plurality of radar pulses to said antenna;
   receiving the plurality of reflected radar pulses from said antenna, using a receiver;
   selecting predetermined ones of the reflected radar pulses received by said receiver, the selected radar pulses corresponding to a predetermined area within the object, the selected pulses representing both internal structure of interest and internal structure contiguous to the structure of interest, the selected pulses discriminating between the internal structure of interest and the contiguous internal structure; and
   displaying a representation of the predetermined area within the object, based on the selected radar pulses.

32. A method according to claim 31, further comprising the step of controlling an aperture of said antenna.

33. A method according to claim 32, further comprising the step of synchronizing said aperture control step, said emitting step, said selecting step, and said displaying step.

34. Apparatus according to claim 31, further comprising the step of producing relative movement between said antenna and the object, and wherein said receiving step includes the step of receiving a plurality of sets of reflected radar pulses, and wherein said selecting step includes the step of selecting radar pulses from among each set, the selected pulses corresponding to a predetermined volume within the object.

35. Radar tomography method, comprising the steps of:
   emitting a plurality of radar pulses toward an object, and receiving a plurality of reflected radar pulses reflected from internal structure within the object, using an antenna;
   filtering the emitted and reflected radar pulses;
   switching said antenna between a transmit mode and a receive mode;
   providing the radar pulses to said antenna;
   receiving the reflected radar pulses from said antenna, using a receiver;
   controlling said receiver to cause only radar pulses reflected from a predetermined area within the object to be received, the selected pulses representing both internal structure of interest and internal structure contiguous to the structure of interest, the selected pulses discriminating between the internal structure of interest and the contiguous internal structure; and causing said predetermined area to be scanned to different locations within the object.

36. A method according to claim 35, further comprising the step of displaying a representation of the predetermined area.

37. A method according to claim 36, further comprising the step of producing relative movement between said antenna and the object, and wherein said emitting step emits a plurality of sets of radar pulses, each set being emitted at a different position, and wherein said controlling step causes said receiver to receive only radar pulses reflected from a predetermined volume within the object.

38. A method according to claim 37, further comprising a processing step for (1) receiving the radar pulses corresponding to the predetermined volume from said receiver, (2) converting these received radar pulses to digital signals, (3) storing the digital signals, and (4) processing the stored digital signals to provide an output signal corresponding to a representation of the predetermined volume.

* * * * *